United States Patent [19]

Darlak

[11] Patent Number: 5,145,655

[45] Date of Patent: Sep. 8, 1992

[54] SURGICAL INSTRUMENT RACK AND FACILITATOR

[76] Inventor: Mariann Darlak, 6 Concord Creek Rd., Glen Mills, Pa. 19342

[21] Appl. No.: 445,268

[22] Filed: Dec. 4, 1989

[51] Int. Cl.$^5$ .......................... A61L 2/26; B01L 9/00
[52] U.S. Cl. ...................................... 422/300; 422/104; 422/297; 211/70.1; 211/70.6; 211/123; 211/133
[58] Field of Search ............... 422/104, 297, 300, 310; 211/70.1, 70.6, 123, 133

[56] References Cited

U.S. PATENT DOCUMENTS

| | | | |
|---|---|---|---|
| 2,018,651 | 10/1935 | Bates | 206/72 |
| 2,903,129 | 9/1959 | Anderson | 206/72 |
| 3,564,662 | 2/1971 | Dold | 21/84 |
| 3,925,014 | 12/1978 | Langdon | 21/105 |
| 4,135,868 | 1/1979 | Schainholz | 422/310 |
| 4,229,420 | 10/1980 | Smith et al. | 422/310 |
| 4,342,391 | 8/1982 | Schainholz | 206/370 |
| 4,541,992 | 9/1985 | Jerge et al. | 422/30 |
| 4,643,303 | 2/1987 | Arp et al. | 206/370 |
| 4,774,063 | 9/1988 | Runnells | 422/297 |
| 4,959,199 | 9/1990 | Brewer | 422/300 |

Primary Examiner—Lynn M. Kummert
Attorney, Agent, or Firm—Don A. Erlandson

[57] ABSTRACT

A support rack for ring handled surgical instruments for use at the incision site in the operating room. The rack comprises an expandable two sectioned interconnected base which allows one half to slide over the other, supports at each end at the top, and a corrugated upper surface. The rack is intended to replace the rolled towel in the sterile field and is useful for keeping the instruments upright and in order, easy to pick up and pass to the surgeon, and for facilitating the before and after count.

1 Claim, 1 Drawing Sheet

SURGICAL INSTRUMENT RACK AND FACILITATOR

SUMMARY OF THE INVENTION

This invention deals generally with materials handling apparatus and particularly those for surgical instruments, such as racks.

Outcomes of surgical operations are directly related to the quality of peri-operative care provided. A professional team utilizes a vast variety of materials. One of the most important of these groups are surgical instruments which are pre-selected, packaged, sterilized and delivered to the operating room. The packages are carefully opened and counted by nurses in gowns, gloves and masks, then arranged in the sterile field which consists of a draped stand known as a mayo table over the surgical site, and a longer larger back table for the specialized instruments. In the average procedure approximately 60 ring handled instruments are positioned on the stand over the incision, almost invariably laid out on a rolled towel; the same way it has been done for about 100 years.

The rolled towel offers no support for the ring handled instruments and they are soon lying flat on each other. In addition to difficulty in removing any one needed instrument from the middle of the pile, such movements often cause another instrument to slide off and out of the field, removing an important tool and affecting the count. If the instrument drops on the floor there is almost certainly damage.

The present invention solves these problems by providing a rigid rack in the shape of an inverted trough, constructed to conform to the shape of ring handled instruments, having two sections connected in a manner which prevents them from being separated and which allows one half to slide over the other; with all upper surfaces being corrugated, and having supports projecting upwardly at each end.

The design of the invention holds the ring handled instruments nearly upright, leaning on each other at a slight angle ready for use. The back side of the rack is curved to accommodate the ring while the top-front slopes downward at approximately a 10° angle; such that the tip of the instrument rests upon the sterile covering of the mayo table. In the preferred embodiment the top front joins a vertical third side which gives the rack added stability. As instruments are withdrawn or added the rack is adjusted by sliding the connected sections closer together or further apart in order to keep the ring handled instruments positioned nearly vertically. The end supports prevent them from dropping, and possible damage. Since speed is an essential in any surgical procedure, keeping the ring handled instruments upright and in order makes them easy to pick up and hand to the surgeon. The corrugated surface minimizes slipping during the movements of selecting and withdrawing. When the final count is taken just before closure of the incision all unused instruments are oriented neatly on the rack, making them easy to identify separately.

In total the present invention provides an adjustable support rack which keeps ring handled instruments upright and in order during surgical operations, easily removable by the nurse to hand to the surgeon since they are oriented almost vertically against each other but do not rest in slots, readily in view at all times to verify the count, and which has end supports to prevent them from sliding out of the field.

DETAILED DESCRIPTION OF THE INVENTION

Figure 1:
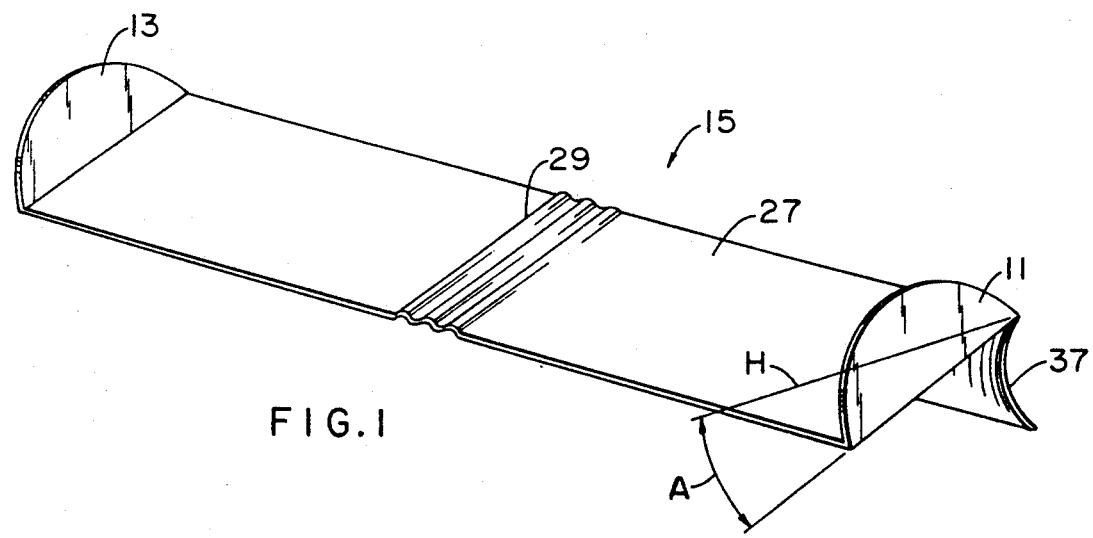
FIG. 1 is a perspective view of an expandable surgical instrument rack embodying the invention. A concave side designed to fit the instrument rings, and end supports are shown.

FIG. 1 pictures an embodiment of the invention, a rack for ring handled surgical instruments comprising a base 15 in the shape of an inverted trough having two or more sides with the base having two upwardly protruding end supports 13, and 11, one at each end.

The inverted trough which forms the base of the instrument rack illustrated in FIG. 1 has a first surface 37 which is concave and essentially vertical, of such curvature as to approximate the shape of a part of the ring of a ring handled surgical instrument, a second surface 27 which meets the first surface at its highest point, with the second surface forming an angle A, to the horizontal plane H in a range of 5 to 20 degrees. The second surface 27 extends downward so that its edge forms a plane with the bottom edge of the first surface.

Second surface 27 of the invention has corrugations 29 along the entire length of the surface to minimize slipping of the instruments. Only a limited number of the corrugations are shown, to preserve clarity of the drawing.

The preferred material of construction of the invention is a light weight polymer such as polypropylene, capable of being sterilized.

An alternative embodiment of the invention has a third surface which meets the second surface at an angle and extends downward vertically such that its bottom edge forms a plane with the bottom edge of the first surface. The base of the alternative embodiment also has two upwardly protruding end supports, one at each end. The three sided base has an advantage of giving more space for the ends of the instruments to rest on the sterile table.

Figure 2:
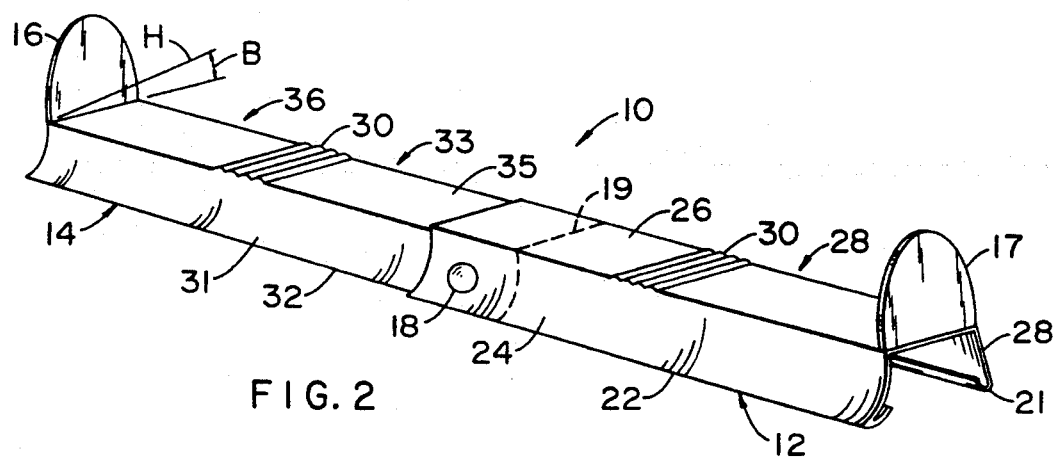
FIG. 2 is a perspective view of an expandable surgical instrument rack with the base constructed with three sides, corrugations along the top, and an automatic stop.
Figure 3:
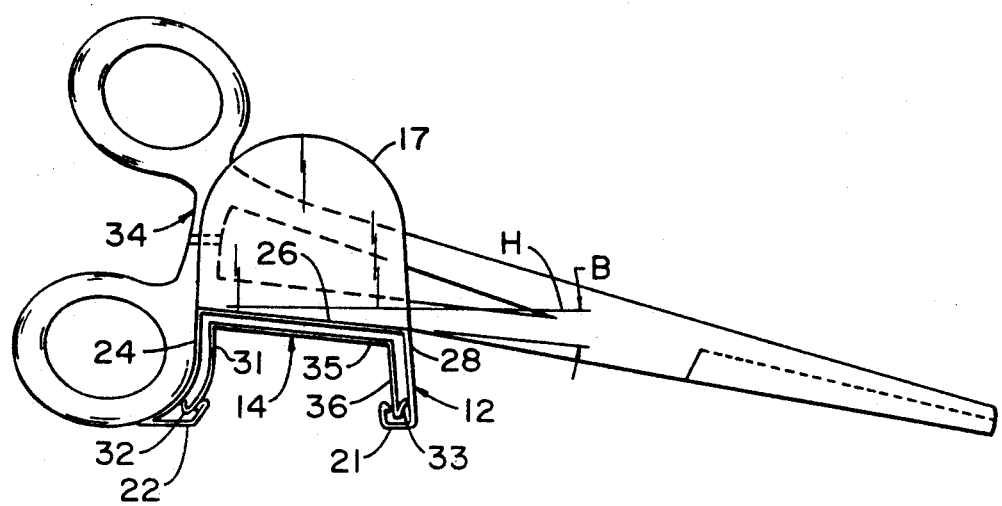
FIG. 3 is an end view of the rack in use supporting an instrument upright. Interconnections of the expandable base are pictured.

FIG. 2 depicts the preferred embodiment of the invention comprising a base 10 comprised of two interconnected sections 12 and 14 forming an entity having essentially continuous surfaces as sides. An embodiment of the interconnecting structure which forms sections 12 and 14 into an entity is shown in FIG. 3.

Interconnected sections 12 and 14 as shown in FIG. 2 are constructed of slightly different dimensions which allow one half to slide over the other, enabling the rack to be manually extended or contracted. The slidable base sections 12 and 14 each have an attached upwardly protruding end support, 17 and 16, respectively.

The entity formed by interconnected base sections 12 and 14 has one or more automatic stops composed of a detent 18 in which a bubble in one section snaps into a window in the other section, when the sections are slid one over the other.

In the preferred embodiment of the invention as shown in FIG. 2, the interconnected sections 12 and 14 of the base 10 are pictured with three sides. A dotted line 19 indicates the end edges of section 14 under section 12. Essentially continuous first surfaces 31 and 24 are concave and essentially vertical, of such curvature as to approximate the shape of a part of the ring of a ring handled surgical instrument. The essentially continuous second surfaces 35 and 26 meet the first surfaces at their highest point, forming an angle B, to the horizontal plane H in a range of 5 to 20 degrees. The second surfaces 35 and 26 have corrugations 30 along the entire length of the surfaces. Only a few corrugations are shown, for clarity. The second surfaces 35 and 26 slope slightly as they extend across and downward and they form angles with the essentially continuous third surfaces 36 and 28. The bottom edges 33 and 21 of third surfaces 36 and 28 form a plane with the bottom edges 32 and 22 of first surfaces 31 and 24, (as best seen in FIG. 3; for clarity, the edges do not touch.)

FIG. 3 is an end view of the preferred embodiment of the invention in which interconnected base sections 12 and 14 are pictured with the three surfaces 24, 26, and 28 of section 12, on the outside, and the three surfaces 31, 35, and 36 of section 14, on the inside. In the preferred embodiment of the interconnecting structure of base section 12 and 14, the bottom edges 21 and 22 of base section 12 are curved inwardly forming a groove and semi-spring which holds another semi-spring formed when bottom edges 32 and 33 of base section 14 are curved outwardly. The connection then comprises an interlocking trough strengthened by tension on both sides. Attached end support 17 is pictured protruding upwardly. In FIG. 3, a ring handled instrument 34 is shown in the manner in which it would rest in the rack.

It is to be understood that the form of this invention as shown is merely a preferred embodiment. Various changes may be made in the function and arrangement of parts; equivalent means may be substituted for those illustrated and described, and certain features may be used independently from others without departing from the spirit and scope of the invention as defined in the claims.

For example the two sided rack of FIG. 1 could be comprised of slidable sections, or the three sided rack of FIG. 2 could have a solid base. In like manner the bottom edges of either section 12 or section 14 of FIGS. 2 and 3 could be left straight, to fit into the groove formed by curling the bottom edges of the other section.

What is claimed as new and for which Letters Patent of the United States are desired to be secured is:

1. A support rack with an exposed top surface for the purpose of holding upright at least one ring handled surgical instrument comprising:

a polymer base member comprising:

a first section with a solid planar top surface oriented in a plane which is located in the range of 5 to 20 degrees from a horizontal plane, the top surface having a first edge, and a second edge parallel to the first edge, and a third edge and fourth edge transverse to the first and second edges; the top surface being corrugated; the first and second edges being the longest edges of the top surface; a solid planar first side surface attached to the top surface at the first edge of the top surface and extending from the plane of the top surface only on one side of the plane of the top surface; a solid curved second side surface attached to the top surface at the second edge of the top surface and extending from the plane of the top surface only on the same side of the plane of the top surface as the first side surface; and a solid planar protrusion permanently attached to the third edge of the top surface and extending from the plane of the top surface on the opposite side of the plane of the top surface as the first and second side surfaces;

a second section with a solid planar top surface oriented in a plane which is located in the range of 5 to 20 degrees from a horizontal plane, the top surface having a first edge, and a second edge parallel to the first edge, and a third edge and fourth edge transverse to the first and second edges; the top surface being corrugated; the first and second edges being the longest edges of the top surface; a solid planar first side surface attached to the top surface at the first edge of the top surface and extending from the plane of the top surface only on one side of the plane of the top surface; a solid curved second side surface attached to the top surface at the second edge of the top surface and extending from the plane of the top surface only on the same side of the plane of the top surface as the first side surface; and a solid planar protrusion permanently attached to the third edge of the top surface and extending from the plane of the top surface on the opposite side of the plane of the top surface as the first and second side surfaces;

and the first and second sections being interconnected adjacent to the fourth edge of the top surface of each section and the first and second sections being constructed of slightly different dimensions one from the other such that the first section slides over the second section enabling the solid planar protrusion of the first section to be moved closer to and further from the solid planar protrusion of the second section; and the top surfaces of the first and second interconnected sections forming an essentially continuous combined top surface;

and the first side surfaces of the first and second interconnected sections forming an essentially continuous solid first combined surface; and the second side surfaces of the first and second interconnected sections forming an essentially continuous solid second combined surface which is concave and essentially vertical and which is of such curvature as to approximate the shape of a part of a ring of a ring handled surgical instrument;

and the first and second interconnected sections having a stop means to prevent the first and second sections from being disconnected, which stop means is composed of a detent with a bubble in the second section which snaps into a window in the first section when the first section is slid over the second section, and the first and second sections further having an interconnection means comprising a groove on each first side surface and each second side surface of each section formed by curling bottom edge of each side surface of each section into a semispring.

* * * * *